(12) United States Patent
Goutsis et al.

(10) Patent No.: US 9,492,366 B2
(45) Date of Patent: *Nov. 15, 2016

(54) DYE GLOSS AGENT WITH SPECIAL CATIONIC PIGMENTS, TENSIDES AND POLYMERS

(71) Applicant: Henkel AG & Co. KGaA, Duesseldorf (DE)

(72) Inventors: Konstantin Goutsis, Juechen (DE); Gabriele Weser, Neuss (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/724,399

(22) Filed: May 28, 2015

(65) Prior Publication Data

US 2015/0257995 A1  Sep. 17, 2015

Related U.S. Application Data

(63) Continuation of application No. PCT/EP2013/074564, filed on Nov. 25, 2013.

(30) Foreign Application Priority Data

Nov. 30, 2012 (DE) .................. 10 2012 221 987

(51) Int. Cl.

| | | |
|---|---|---|
| *A61Q 5/10* | (2006.01) | |
| *A61K 8/41* | (2006.01) | |
| *A61K 8/35* | (2006.01) | |
| *A61K 8/44* | (2006.01) | |
| *A61Q 5/06* | (2006.01) | |
| *A61K 8/81* | (2006.01) | |

(52) U.S. Cl.
CPC .............. *A61K 8/416* (2013.01); *A61K 8/355* (2013.01); *A61K 8/41* (2013.01); *A61K 8/44* (2013.01); *A61K 8/817* (2013.01); *A61Q 5/065* (2013.01); *A61Q 5/10* (2013.01); *A61K 2800/4324* (2013.01); *A61K 2800/5426* (2013.01); *A61K 2800/596* (2013.01)

(58) Field of Classification Search
CPC ........ A61Q 5/10; A61K 8/416; A61K 8/817; A61K 2800/4324; A61K 2800/5426
USPC ............................................................ 8/405
See application file for complete search history.

(56) References Cited

U.S. PATENT DOCUMENTS

| | | |
|---|---|---|
| 5,891,200 A | 4/1999 | Lim et al. |
| 2006/0100114 A1 | 5/2006 | Molenda et al. |

FOREIGN PATENT DOCUMENTS

| | | | |
|---|---|---|---|
| CA | 2613049 | * 4/2008 | .............. A61Q 5/10 |
| CA | 2613049 A1 | 4/2008 | |
| DE | 10144881 A1 | 3/2003 | |
| EP | 0852136 A1 | 7/1998 | |

OTHER PUBLICATIONS

STIC Search Report dated Jul. 19, 2015.*
PCT International Search Report (PCT/EP2013/074564) dated Jun. 10, 2014.
Reich et al., "Light Scattering and Shine Measurements of Human Hair: A Sensitive Probe of the Hair Surface", Journal of the Society of Cosmetic Chemists, vol. 44, pp. 221-234, 1993.

* cited by examiner

*Primary Examiner* — Eisa Elhilo
(74) *Attorney, Agent, or Firm* — P. Scott Smith

(57) ABSTRACT

The invention relates to an agent for dyeing keratinic fibers, particularly human hair, containing in a cosmetic base (a) at least one cationic anthraquinone derivative of formula (I) wherein R1, R2, R3 stand independently of one another for a $C_1$-$C_6$ alkyl group, n stands for an integer from 2 to 8 and $A^-$ for a physiologically compatible anion, (b) at least one further cationic direct dyeing pigment, different from formula (I), (c) at least one amphoteric and/or zwitterionic surfactant and (d) at least one cationic polymer.

19 Claims, No Drawings

DYE GLOSS AGENT WITH SPECIAL CATIONIC PIGMENTS, TENSIDES AND POLYMERS

FIELD OF THE INVENTION

The present invention generally relates to cosmetics, and more particularly relates to agents for dyeing keratinic fibers, in particular human hair, the agents containing specific combinations of cationic anthraquinone dyes with further cationic dyes, with amphoteric or zwitterionic surfactants, and with cationic polymers.

BACKGROUND OF THE INVENTION

Either direct dyes or oxidation dyes are generally used for dyeing keratinic fibers. Although intense coloring with good fastness properties may be achieved with oxidation dyes, the development of the color generally takes place under the influence of oxidizing agents such as $H_2O_2$, which in some cases may result in damage to the fiber. In addition, some oxidation dye precursors or certain mixtures of oxidation dye precursors may have a sensitizing effect in persons with sensitive skin. Direct dyes are applied under milder conditions. However, they have the disadvantage that the colorings have insufficient fastness properties, in particular during washing of the hair, but also with respect to external influences such as sunlight or reactive environmental chemicals, for example swimming pool water. Such colorings are also generally much more sensitive to shampooing than the oxidative colorings, so that an often undesirable change in shade, or even a visible discoloration, then occurs much more quickly.

In addition to an attractive hair color, the consumer also desires lustrous hair. Lustrous hair looks attractive and healthy, and the hairstyle is perceived as being well cared for and full of vitality. In many cases, the consumer has a number of wishes that he/she would like to fulfill at the same time; i.e., the consumer wants an attractive hair color, and also wants lustrous hair. For practical reasons, for this purpose the consumer would prefer to use only one treatment method on the hair.

Various methods are already known from the prior art for coloring the hair in a great variety of shades. A large number of various formulations is disclosed in CA 2613049 A1, for example. However, there is still a need for novel coloring agents which produce intense coloring, and at the same time, exceptionally high luster.

In particular, there is a need for novel coloring agents which are able to produce a long-lasting luster. The hair which is dyed with these agents should not lose its luster after one, or at the most, several, weeks, and instead, its luster should still be noticeable even after multiple hair washings.

BRIEF SUMMARY OF THE INVENTION

Agent for dyeing keratinic fibers, in particular human hair, containing in a cosmetic carrier at least one cationic anthraquinone derivative of formula (I)

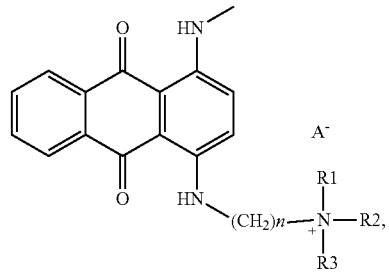

wherein R1, R2, R3 independently stand for a $C_1$-$C_6$ alkyl group, n stands for an integer from 2 to 8, and A stands for a physiologically acceptable anion; at least one further cationic direct dye which is different from formula (I); at least one amphoteric and/or zwitterionic surfactant; and at least one cationic polymer.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The object of the present invention, therefore, is to provide novel direct dyes which intensely color the hair and at the same time impart a very high luster to the hair. The luster of the colorings produced with these agents should be long-lasting, and should persist after multiple hair washings.

Furthermore, other desirable features and characteristics of the present invention will become apparent from the subsequent detailed description of the invention and the appended claims, taken in conjunction with the accompanying drawings and this background of the invention.

It has now surprisingly been found that agents which contain a combination of a specific cationic anthraquinone derivative with a further cationic dye, with an amphoteric or zwitterionic surfactant, and with a cationic polymer, intensely color the hair and at the same time impart a high luster to the hair. Furthermore, the luster produced with these agents is long-lasting, and is still visible even after multiple hair washings or shampoo treatments.

At the same time, these agents also meet all other requirements imposed on the coloring agents for keratinic fibers with regard to their technical application properties, their fastness properties, their toxicological profile, their industrial manufacturability, and their storage stability.

A first subject matter of the present invention relates to an agent for dyeing keratinic fibers, in particular human hair, the agent containing in a cosmetic carrier (a) at least one cationic anthraquinone derivative of formula (I)

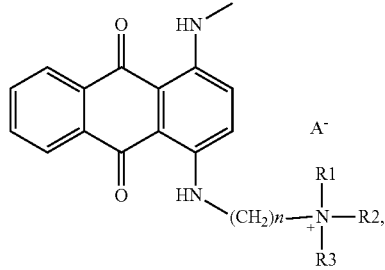

wherein
R1, R2, R3 independently stand for a $C_1$-$C_6$ alkyl group,
n stands for an integer from 2 to 8, and
A stands for a physiologically acceptable anion,
(b) at least one further cationic direct dye which is different from formula (I),
(c) at least one amphoteric and/or zwitterionic surfactant, and
(d) at least one cationic polymer.

Keratinic fibers, also referred to as keratin fibers, are understood to mean fur, wool, feathers, and in particular human hair. Although the agents according to the invention are primarily suited for dyeing keratin fibers, use in other fields is also possible in principle.

The term "agents for dyeing" keratin fibers which is used according to the invention is understood to mean coloring agents which dye the keratin fibers on the basis of direct dyes. In addition, these agents may also contain oxidation dye precursors, so-called developer and coupler components. Developers and couplers diffuse separately into the keratin fiber, and under the influence of an alkalizing agent (ammonia, for example) and an oxidizing agent (usually hydrogen peroxide) form the actual dyes in a chemical reaction with one another. If the agents for dyeing hair contain solely direct dyes, the hair is dyed without at the same time being lightened. However, if the agents additionally contain developer, coupler, and/or oxidizing agent, the keratin fibers are also lightened due to the oxidizing agent that is additionally contained. In the sense of the present invention, a lightening coloring is encompassed by the definition of "coloring."

The agents according to the invention contain the active substances in a cosmetic carrier, preferably in a suitable aqueous, alcoholic, or aqueous-alcoholic carrier. For the purposes of the hair treatment, such carriers are, for example, creams, emulsions, gels, or also surfactant-containing foaming solutions such as shampoos, aerosol foams, foam formulations, or other preparations that are suitable for applying to the hair. However, it is also conceivable to integrate the agents according to the invention into a powdered or also a tablet formulation.

In the sense of the present invention, aqueous-alcoholic solutions are understood to mean aqueous solutions containing 3 to 70% by weight of a $C_1$-$C_4$ alcohol, in particular ethanol or isopropanol. The agents according to the invention may additionally contain further organic solvents such as methoxybutanol, benzyl alcohol, ethyl diglycol, or 1,2-propylene glycol. All water-soluble organic solvents are preferred. In the sense of the invention, the aqueous carrier contains at least 30% by weight, in particular at least 50% by weight, water, based on the total weight of the agents. Aqueous carriers are preferred according to the invention.

As the first important ingredient (a), the agents according to the invention contain at least one cationic anthraquinone derivative of formula (I)

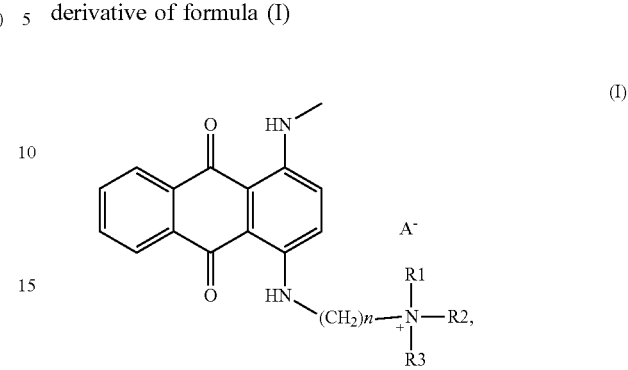

wherein
R1, R2, R3 independently stand for a $C_1$-$C_6$ alkyl group,
n stands for an integer from 2 to 8, and
$A^-$ stands for a physiologically acceptable anion.

In this regard, the radicals R1, R2, and R3 independently stand for a $C_1$-$C_6$ alkyl group.

In one preferred embodiment, R1 and R2 each stand for a methyl group.

In another preferred embodiment, R3 stands for a methyl group, an ethyl group, an n-propyl group, or an isopropyl group.

R1 and R2 in each case very particularly preferably stand for a methyl group, and R3 stands for an n-propyl group.

It is further preferred when n stands for the numbers 2 or 3, and n very particularly preferably stands for the number 3.

$A^-$ stands for a physiologically acceptable anion. Suitable physiologically acceptable anions are halide, hydrogen sulfate, ½ sulfate, benzene sulfonate, p-toluenesulfonate, acetate, citrate, lactate, ½ tartrate, methyl sulfate ($H_3COSO_3^-$), or trifluoromethanesulfonate. $A^-$ particularly preferably stands for bromide or for methyl sulfate ($H_3COSO_3^-$), and $A^-$ very particularly preferably stands for bromide.

One particularly preferred embodiment is an agent for dyeing keratinic fibers, which is characterized in that the agent contains at least one cationic anthraquinone derivative (a) of formula (I), in which
R1 and R2 each stand for a methyl group,
R3 stands for an n-propyl group, and
n stands for the numbers 2 or 3, preferably for the number 3.

Particularly intense and lustrous colorings may be produced when compound (Ia) is used in the agent according to the invention as the cationic anthraquinone derivative of formula (I)

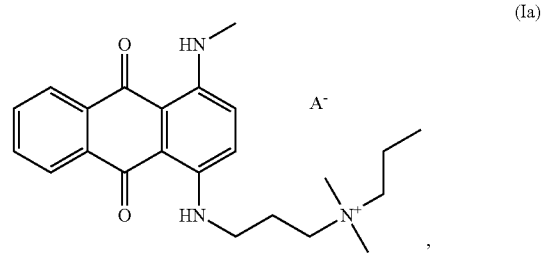

where A⁻ stands for a physiologically acceptable anion, preferably for methyl sulfate ($H_3COSO_3^-$) or bromide, particularly preferably for bromide.

Compound (Ia), in which A⁻ stands for bromide, is also known under the designation HC Blue 16 or Bluequat B, Bluequat bromide, or under the chemical name 3-{[9,10-dihydro-4-(methylamino)-9,10-dioxo-1-anthracenyl]amino}-N,N-dimethyl-N-propyl-1-propanaminium bromide.

The agents according to the invention for dyeing keratin fibers preferably contain the compound(s) of formula (I) in quantities of greater than or equal to 0.0005% by weight and less than or equal to 0.5% by weight, in each case based on the total weight of the agent. The basis for calculations for these quantity statements is in each case the total quantity of all anthraquinone dyes of formula (I) contained in the agent according to the invention.

In one particularly preferred embodiment, an agent according to the invention is characterized in that it contains one or more cationic anthraquinone derivatives of formula (I) in a total quantity of 0.0005 to 0.5% by weight, preferably 0.02 to 0.4% by weight, more preferably 0.05 to 0.3% by weight, and particularly preferably 0.10 to 0.35% by weight, in each case based on the total weight of the agent.

As the second important component, the agent according to the invention contains at least one further cationic direct dye (b) which is different from formula (I). In this regard, a cationic dye is understood to mean a dye having a cationic charge.

This cationic charge may be situated on a quaternary nitrogen atom. Quaternary nitrogen atoms have four different organic radicals, as the result of which the nitrogen atom is positively charged. However, it is likewise possible for the cationic charge to be situated on a nitrogen-containing heterocycle of the direct dye. If this heterocycle is part of the chromophoric system, the positive charge of the direct dye may also be delocalized over the entire chromophoric system. Lastly, it is likewise possible that the cationic dye is a cationic triarylmethane dye, in which the cationic charge is delocalized within the triarylmethane system.

Particularly intense color results may be produced in conjunction with a high, long-lasting luster when the agent according to the invention contains at least one dye from the group Basic Blue 7, Basic Blue 26, Basic Violet 2, Basic Violet 14, Basic Yellow 57, Basic Red 76, Basic Blue 99, Basic Brown 16, Basic Brown 17, Basic Yellow 87, Basic Orange 31, Basic Red 51, and Cationic Blue 347 as the further cationic direct dye (b) which is different from formula (I).

A further particularly preferred embodiment, therefore, is an agent which is characterized in that it contains at least one dye from the group Basic Blue 7, Basic Blue 26, Basic Violet 2, Basic Violet 14, Basic Yellow 57, Basic Red 76, Basic Blue 99, Basic Brown 16, Basic Brown 17, Basic Yellow 87, Basic Orange 31, Basic Red 51, and Cationic Blue 347 as the further cationic direct dye (b) which is different from formula (I).

A further preferred subject matter of the present invention relates to an agent for dyeing keratinic fibers, containing in a cosmetic carrier
(a) Bluequat B as the cationic anthraquinone derivative of formula (I),
(b) Basic Blue 7 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Blue 26 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Violet 2 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Violet 14 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Yellow 57 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Red 76 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Blue 99 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Brown 16 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier (a) Bluequat B as the cationic anthraquinone derivative of formula (I),
(b) Basic Brown 17 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Yellow 87 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Orange 31 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Red 51 as the further cationic direct dye,
(c) at least one amphoteric and/or zwitterionic surfactant, and
(d) at least one cationic polymer.

A further preferred subject matter of the present invention relates to an agent for dyeing keratinic fibers, containing in a cosmetic carrier
(a) Bluequat B as the cationic anthraquinone derivative of formula (I),
(b) Cationic Blue 347 as the further cationic direct dye,
(c) at least one amphoteric and/or zwitterionic surfactant, and
(d) at least one cationic polymer.

Within the above-mentioned group of cationic direct dyes (b) which are different from formula (I), certain specific dyes are characterized in that they may be used to produce colorings having a particularly exceptional luster when, in combination with the other important components (a), (c), and (d), they are used to color keratinic fibers. A particularly high luster may be achieved when at least one compound from the group Basic Yellow 87, Basic Orange 31, Basic Red 51, Basic Violet 2, and Cationic Blue 347 is used as the further cationic direct dye (b).

The highest luster may be obtained with one or more of the compounds from the group Basic Yellow 87, Basic Orange 31, Basic Red 51, Basic Violet 2 in combination with the further important components (a), (c), and (d).

In one explicitly mentioned very particularly preferred embodiment, an agent according to the invention is therefore characterized in that the cationic direct dye(s) (b) which are/is different from formula (I) are/is at least one dye selected from the group Basic Yellow 87, Basic Orange 31, Basic Red 51, Basic Violet 2, and Cationic Blue 347, preferably from the group Basic Yellow 87, Basic Orange 31, Basic Red 51, and Basic Violet 2.

The preferred and particularly preferred cationic direct dyes (b) are the following compounds:

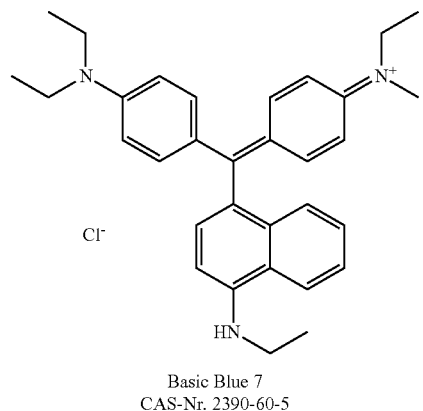

Basic Blue 7
CAS-Nr. 2390-60-5

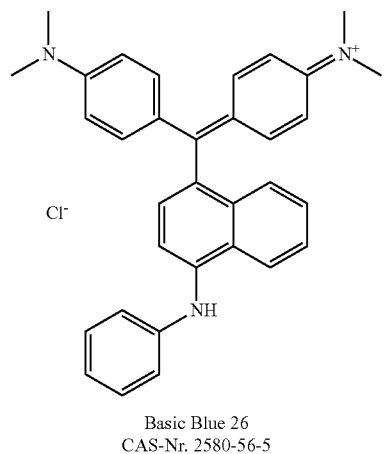

Basic Blue 26
CAS-Nr. 2580-56-5

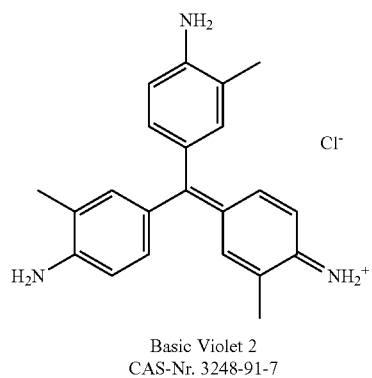

Basic Violet 2
CAS-Nr. 3248-91-7

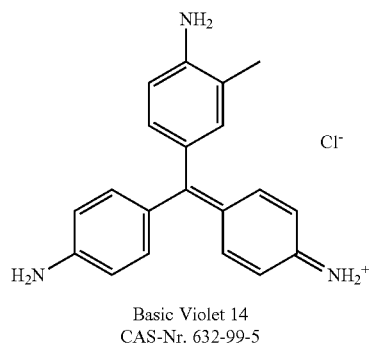

Basic Violet 14
CAS-Nr. 632-99-5

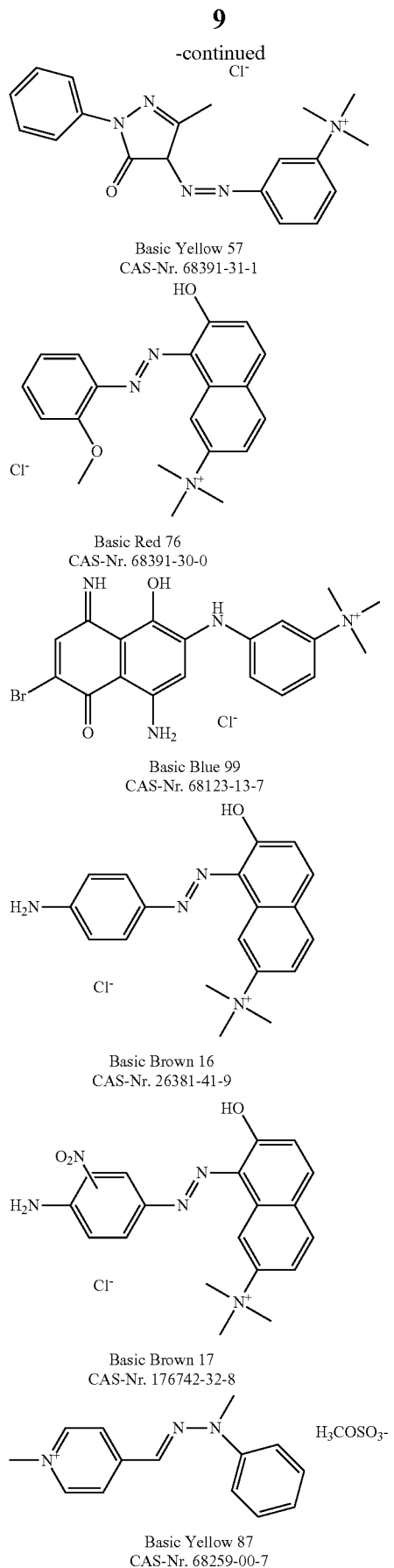

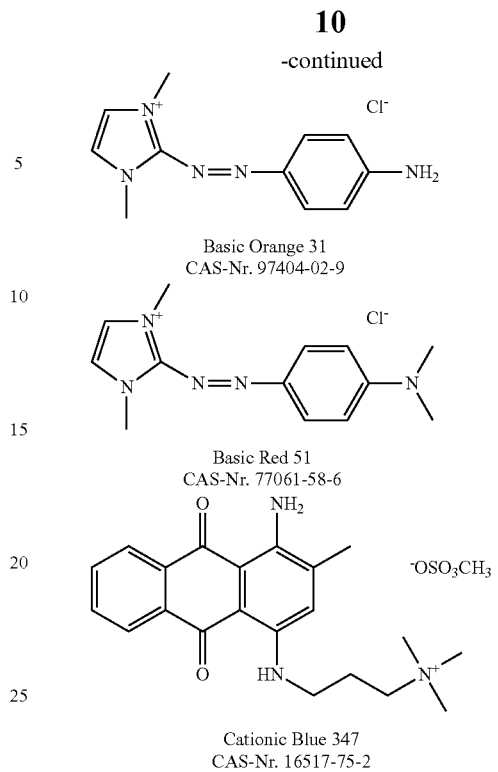

The cationic direct dyes which are different from formula (I) are contained in the agent according to the invention in preferred quantity ranges. The quantities should be selected in such a way that they are great enough to achieve a high luster, but on the other hand small enough to avoid the disadvantages associated with an excessive use concentration of the dyes, such as increased discoloration of the skin or possible skin irritation.

These prerequisites are met when the agents according to the invention contain one or more cationic direct dyes (b) which are different from formula (I) in a total quantity of greater than or equal to 0.0005 and less than or equal to 0.55% by weight, in each case based on the total weight of the agent.

In a further particularly preferred embodiment, an agent according to the invention is characterized in that it contains one or more cationic direct dyes (b), which are different from formula (I), in a total quantity of 0.0005 to 0.55% by weight, preferably 0.005 to 0.40% by weight, more preferably 0.025 to 0.30% by weight, and particularly preferably 0.05 to 0.20% by weight, in each case based on the total weight of the agent.

As the third important component, the agents according to the invention contain at least one amphoteric and/or zwitterionic surfactant (c).

Surfactants are amphiphilic (bifunctional) compounds composed of at least one hydrophobic and at least one hydrophilic molecule portion. The hydrophobic radical is preferably a hydrocarbon chain which contains 8-24 carbon atoms and which may be saturated or unsaturated, linear or branched. This $C_8$-$C_{24}$ alkyl chain is particularly preferably linear.

Basic properties of the surfactants are the targeted absorption to boundary surfaces, as well as the aggregation into micelles and the formation of lyotropic phases.

Amphoteric surfactants are subdivided into ampholytic surfactants and zwitterionic surfactants. Ampholytic surfactants are understood to mean those surface-active compounds which have acidic hydrophilic groups (—COOH or —SO$_3$H groups, for example) and basic hydrophilic groups (amino groups, for example), and which thus have acidic or basic behavior, depending on the conditions. Zwitterionic surfactants are understood by those skilled in the art to mean surfactants which bear both a negative and a positive charge in the same molecule.

Examples of preferred zwitterionic surfactants (c) are betaines, N-alkyl-N,N-dimethylammonium glycinates, N-acyl-aminopropyl-N,N-dimethylammonium glycinates, and 2-alkyl-3-carboxymethyl-3-hydroxyethyl imidazolines, in each case having 8 to 24 C atoms in the alkyl group.

Examples of preferred ampholytic surfactants (c) are N-alkylglycine, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, in each case having 8 to 24 C atoms in the alkyl group.

In another preferred embodiment, an agent according to the invention is therefore characterized in that it contains at least one surfactant from the group of betaines, N-alkyl-N, N-dimethylammonium glycinates, N-acylaminopropyl-N, N-dimethylammonium glycinates, 2-alkyl-3-carboxymethyl-3-hydroxyethyl imidazolines, N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids as the amphoteric and/or zwitterionic surfactant (c).

Further preferred amphoteric and/or zwitterionic surfactants (c) are the surfactants of formulas (II) to (XIII) below.

A further preferred subject matter of the present invention relates to an agent for dyeing keratinic fibers, containing in a cosmetic carrier
(a) at least one cationic anthraquinone derivative of formula (I), where R1, R2, R3, n, and A$^-$ are defined as described above,
(b) at least one further cationic direct dye which is different from formula (I),
(c) at least one amphoteric and/or zwitterionic surfactant of formula (II)

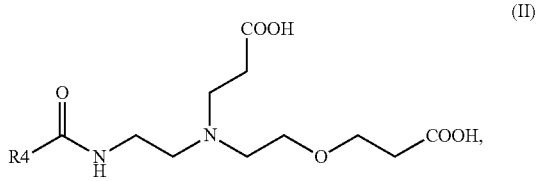

(II)

where R4 stands for a saturated or unsaturated, branched or unbranched C$_8$-C$_{24}$ alkyl group, and
(d) at least one cationic polymer.

A further preferred subject matter of the present invention relates to an agent for dyeing keratinic fibers, containing in a cosmetic carrier
(a) at least one cationic anthraquinone derivative of formula (I), where R1, R2, R3, n, and A$^-$ are defined as described above,
(b) at least one further cationic direct dye which is different from formula (I),
(c) at least one amphoteric and/or zwitterionic surfactant of formula (III)

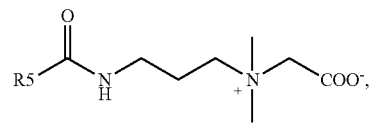

(III)

where R5 stands for a saturated or unsaturated, branched or unbranched C$_8$-C$_{24}$ alkyl group, and
(d) at least one cationic polymer.

A further preferred subject matter of the present invention relates to an agent for dyeing keratinic fibers, containing in a cosmetic carrier
(a) at least one cationic anthraquinone derivative of formula (I), where R1, R2, R3, n, and A$^-$ are defined as described above,
(b) at least one further cationic direct dye which is different from formula (I),
(c) at least one amphoteric and/or zwitterionic surfactant of formula (IV)

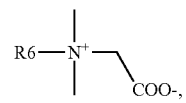

(IV)

where R6 stands for a saturated or unsaturated, branched or unbranched C$_8$-C$_{24}$ alkyl group, and
(d) at least one cationic polymer.

A further preferred subject matter of the present invention relates to an agent for dyeing keratinic fibers, containing in a cosmetic carrier
(a) at least one cationic anthraquinone derivative of formula (I), where R1, R2, R3, n, and A$^-$ are defined as described above,
(b) at least one further cationic direct dye which is different from formula (I),
(c) at least one amphoteric and/or zwitterionic surfactant of formula (V)

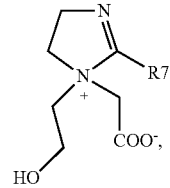

(V)

where R7 stands for a saturated or unsaturated, branched or unbranched C$_8$-C$_{24}$ alkyl group, and
(d) at least one cationic polymer.

A further preferred subject matter of the present invention relates to an agent for dyeing keratinic fibers, containing in a cosmetic carrier
(a) at least one cationic anthraquinone derivative of formula (I), where R1, R2, R3, n, and A$^-$ are defined as described above,
(b) at least one further cationic direct dye which is different from formula (I),
(c) at least one amphoteric and/or zwitterionic surfactant of formula (VI)

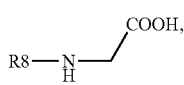
(VI)

where R8 stands for a saturated or unsaturated, branched or unbranched $C_8$-$C_{24}$ alkyl group, and (d) at least one cationic polymer.

A further preferred subject matter of the present invention relates to an agent for dyeing keratinic fibers, containing in a cosmetic carrier (a) at least one cationic anthraquinone derivative of formula (I), where R1, R2, R3, n, and A⁻ are defined as described above, (b) at least one further cationic direct dye which is different from formula (I), (c) at least one amphoteric and/or zwitterionic surfactant of formula (VII)

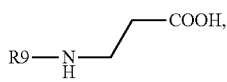
(VII)

where R9 stands for a saturated or unsaturated, branched or unbranched $C_8$-$C_{24}$ alkyl group, and (d) at least one cationic polymer.

A further preferred subject matter of the present invention relates to an agent for dyeing keratinic fibers, containing in a cosmetic carrier (a) at least one cationic anthraquinone derivative of formula (I), where R1, R2, R3, n, and A⁻ are defined as described above, (b) at least one further cationic direct dye which is different from formula (I), (c) at least one amphoteric and/or zwitterionic surfactant of formula (VIII)

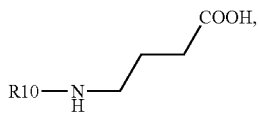
(VIII)

where R10 stands for a saturated or unsaturated, branched or unbranched $C_8$-$C_{24}$ alkyl group, and (d) at least one cationic polymer.

A further preferred subject matter of the present invention relates to an agent for dyeing keratinic fibers, containing in a cosmetic carrier (a) at least one cationic anthraquinone derivative of formula (I), where R1, R2, R3, n, and A⁻ are defined as described above, (b) at least one further cationic direct dye which is different from formula (I), (c) at least one amphoteric and/or zwitterionic surfactant of formula (IX)

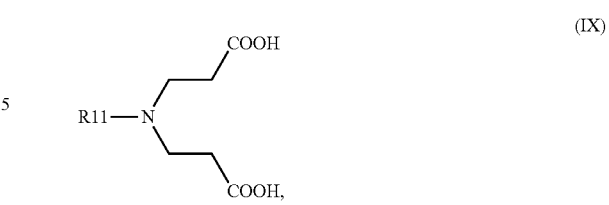
(IX)

where R11 stands for a saturated or unsaturated, branched or unbranched $C_8$-$C_{24}$ alkyl group, and (d) at least one cationic polymer.

A further preferred subject matter of the present invention relates to an agent for dyeing keratinic fibers, containing in a cosmetic carrier (a) at least one cationic anthraquinone derivative of formula (I), where R1, R2, R3, n, and A⁻ are defined as described above, (b) at least one further cationic direct dye which is different from formula (I), (c) at least one amphoteric and/or zwitterionic surfactant of formula (X)

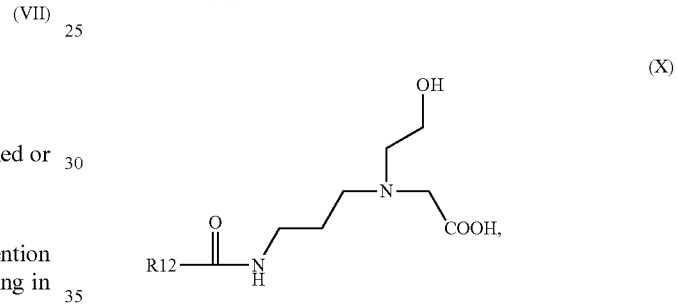
(X)

where R12 stands for a saturated or unsaturated, branched or unbranched $C_8$-$C_{24}$ alkyl group, and (d) at least one cationic polymer.

A further preferred subject matter of the present invention relates to an agent for dyeing keratinic fibers, containing in a cosmetic carrier (a) at least one cationic anthraquinone derivative of formula (I), where R1, R2, R3, n, and A⁻ are defined as described above, (b) at least one further cationic direct dye which is different from formula (I), (c) at least one amphoteric and/or zwitterionic surfactant of formula (XI)

(XI)

where R13 stands for a saturated or unsaturated, branched or unbranched $C_8$-$C_{24}$ alkyl group, and (d) at least one cationic polymer.

A further preferred subject matter of the present invention relates to an agent for dyeing keratinic fibers, containing in a cosmetic carrier (a) at least one cationic anthraquinone derivative of formula (I), where R1, R2, R3, n, and A⁻ are defined as described above, (b) at least one further cationic direct dye which is different from formula (I),
(c) at least one amphoteric and/or zwitterionic surfactant of formula (XII)

where R14 stands for a saturated or unsaturated, branched or unbranched $C_8$-$C_{24}$ alkyl group, and
(d) at least one cationic polymer.

A further preferred subject matter of the present invention relates to an agent for dyeing keratinic fibers, containing in a cosmetic carrier
(a) at least one cationic anthraquinone derivative of formula (I), where R1, R2, R3, n, and $A^-$ are defined as described above,
(b) at least one further cationic direct dye which is different from formula (I),
(c) at least one amphoteric and/or zwitterionic surfactant of formula (XIII)

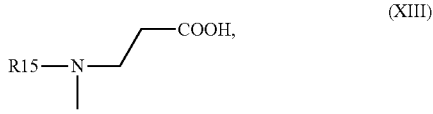

where R15 stands for a saturated or unsaturated, branched or unbranched $C_8$-$C_{24}$ alkyl group, and
(d) at least one cationic polymer.

Within the group of amphoteric and/or zwitterionic surfactants, the compounds of formulas (II) and/or (III) are very particularly preferred, since the highest luster may be produced on keratinic fibers when these compounds are used.

In a further very particularly preferred embodiment, an agent according to the invention is therefore characterized in that it contains at least one compound of formula (II) and/or of formula (III) as the amphoteric and/or zwitterionic surfactant (c)

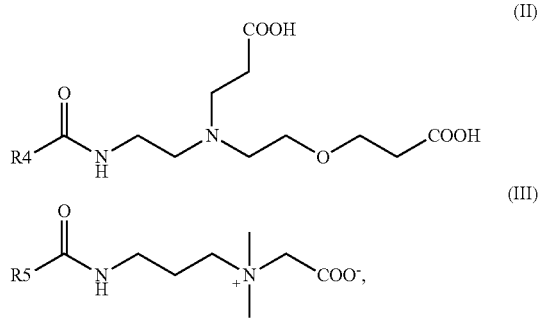

wherein
R4, R5 in each case independently stand for a saturated or unsaturated, branched or unbranched $C_8$-$C_{24}$ alkyl group.

The compounds of structures (II) to (X) as well as (XII) and (XIII) contain carboxylic acid groups. In aqueous medium, carboxylic acid groups eliminate a proton, regardless of the pH of the surrounding medium, and are then in equilibrium with their respective carboxylate anion. In addition to the protonated form (—COOH) of the particular surfactant, the deprotonated form (—COO—) thereof is in accordance with the invention. To ensure electroneutrality, the deprotonated carboxylic acid may also be present in the form of its respective salt, preferably its alkali metal (Na, K) salt.

For achieving the stated object of the invention, very particularly suited amphoteric and/or zwitterionic surfactants of formula (II) are the compounds known under the INCI name disodium cocoamphodipropionate.

For achieving the stated object of the invention, very particularly suited amphoteric and/or zwitterionic surfactants of formula (III) are the compounds known under the INCI name cocamidopropyl betaine.

The amphoteric and/or zwitterionic surfactants (c) are preferably contained in the agents according to the invention in certain quantity ranges. The basis for calculations for the quantity statements given below is the total quantity of all amphoteric surfactants and zwitterionic surfactants contained in the particular agent, wherein the quantities in each case are based on the total weight of the agent.

In another preferred embodiment, an agent according to the invention is characterized in that it contains one or more amphoteric and/or zwitterionic surfactants (c) in a total quantity of 0.1 to 4.0% by weight, preferably 0.2 to 2.5% by weight, more preferably 0.4 to 1.8% by weight, and particularly preferably 0.6 to 0.9% by weight, in each case based on the total weight of the agent.

As the fourth important component, the agents according to the invention contain at least one cationic polymer (d).

Polymers are understood to mean macromolecules having a molecular weight of at least 1000 g/mol, preferably at least 2500 g/mol, particularly preferably at least 5000 g/mol, and which consist of identical repeating organic units. Polymers are produced by polymerization of one monomer type, or by polymerization of various monomer types which are structurally different from one another. If the polymer is produced by polymerization of one monomer type, it is referred to as a homopolymer. If structurally different monomer types are used in the polymerization, the resulting polymer is referred to as a copolymer.

The maximum molecular weight of the polymer depends on the degree of polymerization (the number of polymerized monomers), and is determined by the polymerization method. In the sense of the present invention, it is preferred when the maximum molecular weight of the cationic polymer (d) is not greater than $10^7$ g/mol, preferably not greater than $10^6$ g/mol, and particularly preferably not greater than $10^5$ g/mol.

Cationic polymers are understood to mean those polymers which contain cationic groups in the macromolecule (polymer). These cationic groups contained in the macromolecule (polymer) are quaternary ammonium groups.

In the course of the studies leading to the present invention, it has been shown that particularly intense colorings and high luster values may be achieved when specific cationic polymers together with the further important components (a), (b), and (c) are used in a formulation.

A particularly high and long-lasting luster may be achieved when at least one polymer from the group Polyquaternium-2, Polyquaternium-5, Polyquaternium-6, Polyquaternium-7, Polyquaternium-8, Polyquaternium-9, Polyquaternium-11, Polyquaternium-16, Polyquaternium-28, Polyquaternium-32, Polyquaternium-33, Polyquaternium-44, Polyquaternium-46, Polyquaternium-55, and Polyquaternium-68 is contained as cationic polymer (d) in the agent according to the invention.

In another particularly preferred embodiment, an agent according to the invention is therefore characterized in that it contains at least one polymer from the group Polyquaternium-2, Polyquaternium-5, Polyquaternium-6, Polyquaternium-7, Polyquaternium-8, Polyquaternium-9, Polyquaternium-11, Polyquaternium-16, Polyquaternium-28, Polyquaternium-32, Polyquaternium-33, Polyquaternium-44, Polyquaternium-46, Polyquaternium-55, and Polyquaternium-68 as cationic polymer (d).

Polyquaternium-2 is poly[oxy-1,2-ethanediyl(dimethyliminio)-1,3-propanediyliminocarbonylimino-1,3-propanediyl(dimethyliminio)-1,2-ethanediyl chloride (1:2), which is marketed under the trade names Lugalvan P or Mirapol A 15, for example.

Polyquaternium-5 is a copolymer of N,N,N-trimethyl-2-[(2-methyl-1-oxo-2-propen-1-yl)oxy]ethanaminium methyl sulfate and 2-propenamide, and is marketed under the trade names Calgon K 400, Catamer Q, Hercofloc 812, or Merquat 5, for example.

Polyquaternium-6 is the homopolymer of N,N-dimethyl-N-(2-propen-1-yl)-2-propen-1-aminium chloride, and is available under the trade names Merquat 100 or Genamin PDAC, for example.

Polyquaternium-7 is the copolymer of N,N-dimethyl-N-(2-propen-1-yl)-2-propen-1-aminium chloride and 2-propenamide, and is marketed under the trade names Merquat 550, Merquat 2220, or Rheocare CC7, for example.

Polyquaternium-8 is the copolymer of 2-methyl-2-propenoic acid methyl ester, 2-(dimethylamino)ethyl-2-methyl-2-propenoate, and octadecyl-2-methyl-2-propenoate which has been quaternized with dimethyl sulfate.

Polyquaternium-9 is the homopolymer of 2-(dimethylamino)ethyl-2-methyl-2-propenoate which has been quaternized with methyl bromide.

Polyquaternium-11 is the copolymer of 2-methyl-2-propenoic acid-2-(dimethylamino)ethyl ester and 1-ethenyl-2-pyrrolidinone which has been quaternized with diethyl sulfate. Polyquaternium-11 is marketed under the trade names Celquat 200, Gafquat 755, or Luviquat PQ 11, for example.

Polyquaternium-16 is the copolymer of 1-ethenyl-2-pyrrolidinone and 1-ethenyl-3-methyl-1H-imidazolium chloride, and is marketed under the trade names Luviquat FC 500, Luviquat FC 550, or Luviquat HM 552, for example.

Polyquaternium-28 is a copolymer of N,N,N-trimethyl-3-[(2-methyl-1-oxo-2-propen-1-yl)amino]-1-propanaminium chloride and 1-ethenyl-2-pyrrolidinone, and is available under the trade names Gafquat HS 100 or Conditioneze NF 20, for example.

Polyquaternium-32 is a copolymer of 2-propenamide and N,N,N-trimethyl-2-[(2-methyl-1-oxo-2-propen-1-yl)oxy]ethanaminium chloride, and is marketed under the trade names Salcare SC 92 or Rohagit KF 720F, for example.

Polyquaternium-33 is a copolymer of 2-propenamide and N,N,N-trimethyl-2-[(1-oxo-2-propen-1-yl)oxy]ethanaminium chloride, which is known under the trade names Nalco 1460, Organopol 6400, or Salcare SC 93, for example.

Polyquaternium-44 is a copolymer of 1-ethenyl-3-methyl-1H-imidazolium methyl sulfate and 1-ethenyl-2-pyrrolidinone, and is known under the trade names Luviquat Care or Luviquat MS 370, for example.

Polyquaternium-46 is a copolymer of 1-ethenyl-2-pyrrolidinone, 1-ethenyl-3-methyl-1H-imidaolium methyl sulfate, and 1-ethenylhexahydro-2H-azepin-2-one.

Polyquaternium-55 is a copolymer of 1-ethenyl-2-pyrrolidinone, N-[3-(dimethylamino)propyl]-2-methyl-2-propenamide, and N,N-dimethyl-N-{3-[(2-methyl-1-oxo-2-propen-1-yl)amino]propyl}-1-dodecanaminium chloride, and is marketed under the trade names Styleze W 10 or Styleze W 20, for example.

Lastly, Polyquaternium-68 is a copolymer of 1-ethenyl-3-methyl-1H-imidazolium methyl sulfate, 1-ethenyl-1H-imidazole, 1-ethenyl-2-pyrrolidinone, and 2-methyl-2-propenamide.

For optimally achieving the stated object of the invention, the agents according to the invention also contain the cationic polymers (d) in preferred quantity ranges.

In another preferred embodiment, an agent according to the invention is therefore characterized in that it contains one or more cationic polymers (d) in a total quantity of 0.1 to 2.0% by weight, preferably 0.2 to 1.3% by weight, more preferably 0.3 to 0.9% by weight, and particularly preferably 0.4 to 0.8% by weight, in each case based on the total weight of the agent.

By far the best luster values have been obtained when Polyquaternium-6 together with the other important components (a), (b), and (c) are used as cationic polymer (d) in the agent according to the invention.

In another explicitly mentioned very particularly preferred embodiment, an agent according to the invention is therefore characterized in that it contains Polyquaternium-6 in a quantity of 0.0001 to 10% by weight, preferably 0.001 to 8% by weight, more preferably 0.01 to 5% by weight, and particularly preferably 0.05 to 2.5% by weight, in each case based on the total weight of the agent, as cationic polymer (d).

A further preferred subject matter of the present invention relates to an agent for dyeing keratinic fibers, containing in a cosmetic carrier
(a) Bluequat B as the cationic anthraquinone derivative of formula (I),
(b) Basic Blue 7 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Blue 7 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Blue 26 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Violet 2 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Violet 14 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Yellow 57 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Red 76 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Blue 99 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Brown 16 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Brown 17 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Yellow 87 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Orange 31 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Basic Red 51 as the further cationic direct dye,
(c) at least one amphoteric and/or zwitterionic surfactant, and
(d) Polyquaternium-6 as the cationic polymer.

A further preferred subject matter of the present invention relates to an agent for dyeing keratinic fibers, containing in a cosmetic carrier
(a) Bluequat B as the cationic anthraquinone derivative of formula (I),
(b) Cationic Blue 347 as the further cationic direct dye,
(c) at least one amphoteric and/or zwitterionic surfactant, and
(d) Polyquaternium-6 as the cationic polymer.

In addition to the cationic anthraquinone dyes of formula (I) and the further cationic dyes (b) which are different from formula (I), the agents according to the invention may contain even further nonionic and/or anionic direct dyes as optional components.

Preferred anionic direct dyes are the compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

In particular nonionic nitro dyes and quinone dyes, and neutral azo dyes, are suited as nonionic direct dyes. Preferred nonionic direct dyes are the compounds known under the international designations or trade names HC Yellow 2, HC Yellow 4, HC Yellow 5, HC Yellow 6, ITC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, in addition to 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxalin, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

Furthermore, the agents according to the invention may also be used as oxidation dyes. Such oxidation dyes additionally contain at least one oxidation dye precursor, preferably at least one oxidation dye precursor of the developer type, and at least one oxidation dye precursor of the coupler type. Particularly suitable oxidation dye precursors of the developer type are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl) methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and physiologically acceptable salts thereof.

Particularly suitable oxidation dye precursors of the coupler type are selected from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl) amino-2-methylphenol, 2,4-dichloro-3-aminophenol, 2-aminophenol, 3-phenylenediamine, 2-(2,4-diaminophenoxyl)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethy)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-yl-phenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or physiologically acceptable salts thereof.

In one preferred embodiment, however, the agents according to the invention are free of oxidation dye precursors.

The optionally contained additional nonionic and/or anionic direct dyes, developer components, and coupler components are preferably used in each case in a quantity of 0.0001 to 5.0% by weight, preferably 0.001 to 2.5% by weight, in each case based on the ready-to-apply agent. Developer components and coupler components are generally used in approximately molar quantities with respect to one another. When the molar use has also proven to be practical, a certain excess of individual oxidation dye precursors is not disadvantageous, so that developer components and coupler components may be present in a molar ratio of 1:0.5 to 1:3, in particular 1:1 to 1:2.

In the case of oxidation dyes, the agents additionally contain an oxidizing agent, preferably hydrogen peroxide. The quantities of hydrogen peroxide correspond to the quantities in the lightening agents according to the invention.

The agents may also be used as lightening coloring agents. To achieve the lightening effect, the agents contain hydrogen peroxide and/or one of the solid addition products thereof with organic or inorganic compounds.

In a further embodiment, an agent according to the invention is therefore characterized in that it additionally contains hydrogen peroxide and/or one of the solid addition products thereof with organic or inorganic compounds.

In one preferred embodiment, hydrogen peroxide itself is used as aqueous solution. The concentration of a hydrogen peroxide solution in the agent according to the invention is determined on the one hand by the regulatory requirements, and on the other hand by the desired effect; 6 to 12% by weight solutions in water are preferably used. Ready-to-apply agents of the first subject matter of the invention which are preferred according to the invention are characterized in that, based on the total weight of the ready-to-apply agent, they contain 0.5 to 20% by weight, preferably 1 to 12.5% by weight, particularly preferably 2.5 to 10% by weight, and in particular 3 to 6% by weight of hydrogen peroxide, in each case based on the total weight of the agent.

To achieve an enhanced lightening and bleaching action, the agent may additionally contain at least one peroxo salt. Suitable peroxo salts are inorganic peroxo compounds, preferably selected from the group comprising ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates are particularly preferred, in particular ammonium peroxodisulfate, potassium peroxodisulfate, and sodium peroxodisulfate.

Persulfates are contained in the agent according to the invention in each case in a quantity of 0.5 to 20% by weight, preferably 1 to 12.5% by weight, particularly preferably 2.5 to 10% by weight, and in particular 3 to 6% by weight, based on the total weight of the ready-to-apply agent.

Another preferred embodiment is an agent for dyeing and optionally lightening keratinic fibers, which additionally contains hydrogen peroxide, one of the solid addition products thereof with organic or inorganic compounds, ammonium peroxodisulfate, potassium peroxodisulfate, and/or sodium peroxodisulfate, in each case in a quantity of 0.5 to 20% by weight, preferably 1 to 12.5% by weight, particularly preferably 2.5 to 10% by weight, and in particular 3 to 6% by weight, based on the total weight of the ready-to-apply agent.

The agent may contain further bleach boosters for enhancing the blonding effect, such as tetraacetylethylenediamine (TAED), 1,5-diacetyl-2,4-dioxohexahydro-1,3,5-triazine (DADHT), tetraacetylglycoluril (TAGU), N-nonanoyl succinimide (NOSI), n-nonanoyl- or isononanoyloxybenzene-sulfonate (n- or iso-NOBS), phthalic acid anhydride, triacetin, ethylene glycol diacetate, and 2,5-diacetoxy-2,5-dihydrofuran, and carbonate salts or hydrogen carbonate salts, in particular ammonium hydrogen carbonate, ammonium carbonate, sodium hydrogen carbonate, disodium carbonate, potassium hydrogen carbonate, dipotassium carbonate, and calcium carbonate, and nitrogen-containing heterocyclic bleach boosters such as 4-acetyl-1-methylpyridinium-p-toluenesulfonate, 2-acetyl-1-methylpyridinium-p-toluenesulfonate, and N-methyl-3,4-dihydroisoquinolinium-p-toluenesulfonate.

For further enhancing the lightening, at least one $SiO_2$ compound, such as silicic acid or silicates, in particular water glasses, may be added to the composition according to the invention. It may be preferred according to the invention to use the $SiO_2$ compounds in quantities of 0.05% by weight to 15% by weight, particularly preferably in quantities of 0.15% by weight to 10% by weight, and very particularly preferably in quantities of 0.2% by weight to 5% by weight, in each case based on the water-free composition according to the invention. The quantity statements in each case reflect the content of the $SiO_2$ compounds (without their water portion) in the agents.

The ready-to-apply coloring agents may further contain additional active substances, auxiliary substances, and additives to improve the coloring power and to adjust other desired properties of the agents.

The ready-to-apply coloring agents are preferably provided as a liquid preparation, and therefore a further surface-active substance is added to the agents, wherein such surface-active substances are referred to as surfactants or as emulsifiers, depending on the field of application: They are preferably selected from anionic, cationic, and nonionic surfactants.

In addition to the amphoteric and/or zwitterionic surfactants (c), the agents according to the invention may additionally contain at least one anionic surfactant. Preferred anionic surfactants are fatty acids, alkyl sulfates, alkyl ether sulfates, and ether carboxylic acids containing 10 to 20 C atoms in the alkyl group and up to 16 glycol ether groups in the molecule. The additional anionic surfactants are used in proportions of 0.1 to 45% by weight, preferably 1 to 30% by weight, and very particularly preferably 1 to 15% by weight, based on the total quantity of the ready-to-apply agent.

At least one nonionic surfactant may additionally be contained in the agent according to the invention. In particular addition products of ethylene oxide and/or propylene oxide with fatty alcohols, fatty acids, fatty acid amides, polyol esters of fatty acids and polyol ethers of fatty alcohols, and alkyl polyglucosides are suitable as nonionic surfactants. Examples of suitable nonionic surfactants are Laureth-2, Beheneth-10, Ceteareth-12, Trideceth-12, Oleth-16, Ceteareth-20, Ceteareth-30, and Ceteareth-50, as well as PPG-1 Trideceth-6, PEG-7 Oleate, PEG-90 Stearate, PEG-30 Cocoate, Polysorbate-20, Polysorbate-60, Polysorbate-65, Polysorbate-80, Polysorbate-85, lauryl glucoside, decyl glucoside, and/or coco glucoside.

The nonionic surfactants are used in quantities of 0.01 to 45% by weight, preferably 0.1 to 30% by weight, and very particularly preferably 1 to 15% by weight, based on the total quantity of the ready-to-apply agents.

Agents which are suitable according to the invention may also contain cationic surfactants of the quaternary ammonium compound, esterquat, and amidoamine types. Preferred quaternary ammonium compounds are ammonium halides and the imidazolium compounds known under the INCI names Quaternium-27 and Quaternium-83. Further cationic surfactants which are usable according to the invention are quaternized protein hydrolysates. Stearamidopropyl dimethylamine, which is commercially available under the name Tegoamid® S 18, is a compound from the amidoamines that is particularly suitable according to the invention. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. The cationic surfactants are preferably contained in the agents used according to the invention in quantities of 0.05 to 10% by weight, based on the overall agent.

The ready-to-apply agents may contain additional auxiliary substances and additives. It has proven to be advantageous when the agents contain at least one thickener. There are no restrictions in principle with regard to these thickeners. Organic as well as strictly inorganic thickeners may be used.

Suitable thickeners are cationic synthetic polymers;

anionic synthetic polymers, such as polyacrylates, acrylate copolymer, copolymers of acrylic acid and methacrylic acid;

naturally occurring thickeners, such as nonionic guar gums, scleroglucan gums, or gum arabic, gum ghatti, karaya gum, gum tragacanth, carrageenan gum, locust bean gum, pectins, xanthans, alginate, starch fractions and derivatives such as amylose, amylopectin, and dextrins, and cellulose derivatives such as carboxymethylcellulose, methylcellulose, and hydroxyalkylcellulose;

nonionic, fully synthetic polymers such as polyvinyl alcohol or polyvinylpyrrolidinone; and inorganic thickeners, in particular layered silicates such as bentonite, in particular smectites such as montmorillonite or hectorite.

Dyeing processes on keratin fibers customarily take place in the slightly acidic to alkaline range, preferably in a slightly acidic to slightly alkaline environment. However, to protect the keratin fibers and also the skin to the greatest extent possible, setting an excessively high pH is not desirable. The pH of the agents according to the invention may therefore be between 3 and 11, preferably between 5 and 8. pH values in the sense of the present invention are pH values that have been measured at a temperature of 22° C.

The alkalizing agents that are usable according to the invention for setting the preferred pH are preferably selected from ammonia, alkanolamines, basic amino acids, and inorganic alkalizing agents. Preferred inorganic alkalizing agents are magnesium carbonate, sodium hydroxide, potassium hydroxide, sodium silicate, and sodium metasilicate. Organic alkalizing agents that are usable according to the invention are preferably selected from monoethanolamine, 2-amino-2-methylpropanol, and triethanolamine. The basic amino acids that are usable as alkalizing agents according to the invention are preferably selected from the group comprising arginine, lysine, ornithine, and histidine, particularly preferably arginine. Acidifying agents that are usable for setting the pH are organic acids such as citric acid, acetic acid, ascorbic acid, benzoic acid, lactic acid, malic acid, and maleic acid, and mineral acids such as hydrochloric acid, sulfuric acid, or phosphoric acid.

Furthermore, it has proven to be advantageous when the coloring agents, in particular when they additionally contain hydrogen peroxide, contain at least one stabilizer or complexing agent. Particularly preferred stabilizers are phenacetin, alkali benzoates (sodium benzoate), and salicylic acid. In addition, all complexing agents of the prior art may be used. Complexing agents preferred according to the invention are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or sodium salts thereof.

In addition, the agents according to the invention may contain further active substances, auxiliary substances, and additives, for example nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or nonvolatile, straight-chain, branched, or cyclic, crosslinked or noncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane (A)-polyoxyalkylene (B) block copolymers, grafted silicone polymers; cationic polymers such as quaternized cellulose ethers, polysiloxanes having quaternary groups, zwitterionic and amphoteric polymers such as Polyquaternium-22 and Polyquaternium-39 in particular; structurizers such as glucose, maleic acid, and lactic acid, hair conditioning compounds such as phospholipids, for example lecithin and cephalins; fragrance oils, dimethyl isosorbide, and cyclodextrins; fiber structure-improving active substances, in particular mono-, di-, and oligosaccharides such as glucose, galactose, fructose, fruit sugar, and lactose; dyes for coloring the agent; anti-dandruff active substances such as piroctone olamines, zinc omadines, and climbazole; amino acids and oligopeptides; animal- and/or plant-based protein hydrolysates, and in the form of their fatty acid condensation products or optionally anionically or cationically modified derivatives; plant oils; light protection agents and UV blockers; active substances such as panthenol, pantothenic acid, pantolactone, allantoin, pyrrolidinone carboxylic acids and salts thereof, and bisabolol; polyphenols, in particular hydroxycinnamic acids, 6,7-dihydroxycoumarin, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling agents and penetration agents such as glycerin, propylene glycol monoethyl ether, carbonates, hydrogen carbonates, guanidines, ureas, and primary, secondary, and tertiary phosphates; opacifiers such as latex, styrene/PVP and styrene/acrylamide copolymers; pearlescence agents such as ethylene glycol mono- and distearate and PEG-3-distearate; pigments, and propellants such as propane-butane mixtures, N2O, dimethyl ether, CO2, and air.

Those skilled in the art will select these further substances according to the desired properties of the agents. With regard to further optional components and the quantities of these components used, explicit reference is made to relevant handbooks known to those skilled in the art, for example Kh. Schrader, Grundlagen and Rezepturen der Kosmetika [Fundamentals and Formulations of Cosmetics], 2nd Edition, Hüthig Buch Verlag, Heidelberg, 1989. The additional active substances and auxiliary substances are preferably used in the agents according to the invention in each case in quantities of 0.0001 to 25% by weight, in particular 0.0005 to 15% by weight, based on the total weight of the application mixture.

For using the agent according to the invention, in particular a method for dyeing and optionally lightening of keratinic fibers, in particular human hair, is suitable which is characterized in that an agent of the first subject matter of the invention is applied to the keratin-containing fibers, left on the fibers for 5 to 60 minutes, and subsequently rinsed out with water or washed out with a shampoo. The exposure period for the ready-to-apply coloring agent is preferably 5 to 45 min, in particular 10 to 40 min, particularly preferably 15 to 35 min. During the exposure period of the agent on the fiber, it may be advantageous to assist the lightening operation by supplying heat. Heat may be supplied via an external heat source, such as hot air from a hot air blower, and, in particular for hair lightening on living subjects, also via the body temperature of the subject. In the latter option, the area to be lightened is customarily covered with a hood. An exposure phase at room temperature is likewise in accordance with the invention. In particular, the temperature during the exposure period is between 20° C. and 40° C., in particular between 25° C. and 38° C. After conclusion of the exposure period, the remaining color preparation is rinsed from the hair with water or a cleaning agent. In particular standard shampoo may be used as cleaning agent, in which case in particular the cleaning agent may be dispensed with, and the rinsing operation may take place using water when the coloring agent has a strong surfactant-containing carrier.

The agents according to the invention may be formulated and appropriately used as one-component agents (coloring and lightening agents) or as multi-component agents, such as two-component agents or three-component agents. Separation into multicomponent systems is useful in particular where there is an expectation of or concern for incompatibilities of the ingredients; in such systems, the agent to be used is prepared by the consumer directly before application by mixing the components.

If the agent according to the invention contains direct dyes, and optionally also oxidation dye precursors as well as oxidizing agent, to prevent a premature, undesirable reaction of these substances with one another, they are advantageously packaged separately, and brought into contact only immediately before use.

A dyeing method in which the coloring cream and the oxidizing agent are initially present in separate form is therefore preferred. A further subject matter of the present invention therefore relates to a method for dyeing and lightening human hair, in which a water-based composition containing hydrogen peroxide is mixed with an agent according to the invention containing the important components (a), (b), (c), and (d) to produce a homogeneous composition, which is applied to the hair.

The formulation containing a combination of
(a) at least one cationic anthraquinone derivative of formula (I)

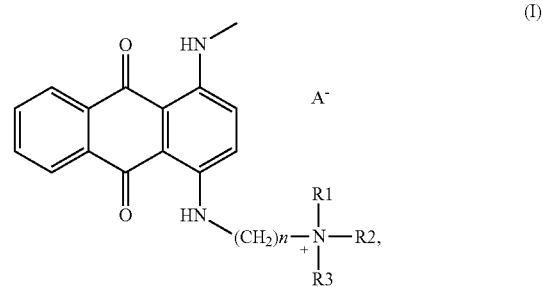

wherein
R1, R2, R3 independently stand for a $C_1$-$C_6$ alkyl group,
n stands for an integer from 2 to 8, and
$A^-$ stands for a physiologically acceptable anion,
(b) at least one further cationic direct dye which is different from formula (I),
(c) at least one amphoteric and/or zwitterionic surfactant, and
(d) at least one cationic polymer,
is very well suited for producing intense colorings having a high, long-lasting luster on keratinic fibers.

A further subject matter of the present invention relates to the use of an agent of the first subject matter of the invention for producing hair colorings having an enhanced, long-lasting luster.

The statements concerning the agents according to the invention similarly apply with regard to further preferred embodiments of the method according to the invention.

EXAMPLES

The following formulations were produced. Quantities are understood to be expressed in each case in percent by weight and the active substance used, unless noted otherwise.

|  | V1 | V2 | V3 | V4 |
|---|---|---|---|---|
| Lorol $C_{12}$-$C_{18}$ technical grade ($C_{12}$-$C_{18}$ fatty alcohols) | 6.0 | 6.0 | 6.0 | 6.0 |
| Lanette D (cetearyl alcohol) | 12.0 | 12.0 | 12.0 | 12.0 |
| Propylparaben | 0.19 | 0.19 | 0.19 | 0.19 |
| Methylparaben | 0.4 | 0.4 | 0.4 | 0.4 |
| Cocoamphodipropionate, disodium salt | 0.72 | 0.72 | 0.72 | 0.72 |
| Ceteareth-20 | 0.9 | 0.9 | 0.9 | 0.9 |
| Bluequat B | — | — | — | — |
| Basic Red 51 | — | 0.2 | 0.1 | — |
| Basic Yellow 87 | 0.2 | — | — | — |
| Basic Orange 31 | 0.04 | — | 0.2 | — |
| Basic Violet 2 | — | — | — | 0.1 |
| Polyquaternium-6 | 0.5 | 0.5 | 0.5 | 0.5 |
| Monoethanolamine | 0.02 | 0.02 | 0.02 | 0.02 |
| Hydroxyethane-1,1-diphosphonic acid | 0.012 | 0.012 | 0.012 | 0.012 |
| Distilled water | ad 100% | ad 100% | ad 100% | ad 100% |

|  | E1 | E2 | E3 | E4 |
|---|---|---|---|---|
| Lorol $C_{12}$-$C_{18}$ technical grade ($C_{12}$-$C_{18}$ fatty alcohols) | 6.0 | 6.0 | 6.0 | 6.0 |
| Lanette D (cetearyl alcohol) | 12.0 | 12.0 | 12.0 | 12.0 |
| Propylparaben | 0.19 | 0.19 | 0.19 | 0.19 |
| Methylparaben | 0.4 | 0.4 | 0.4 | 0.4 |
| Cocoamphodipropionate, disodium salt | 0.72 | 0.72 | 0.72 | 0.72 |
| Ceteareth-20 | 0.9 | 0.9 | 0.9 | 0.9 |
| Bluequat B | 0.4 | 0.285 | 0.15 | 0.05 |
| Basic Red 51 | 0.005 | — | — | — |
| Basic Yellow 87 | — | 0.025 | 0.15 | — |
| Basic Orange 31 | — | — | — | — |
| Basic Violet 2 | — | — | — | 0.0875 |
| Polyquaternium-6 | 0.5 | 0.5 | 0.5 | 0.5 |
| Monoethanolamine | 0.02 | 0.02 | 0.02 | 0.02 |
| Hydroxyethane-1,1-diphosphonic acid | 0.012 | 0.012 | 0.012 | 0.012 |
| Distilled water | ad 100% | ad 100% | ad 100% | ad 100% |

The luster of hair strands dyed blond (Kerling, dyed blond 1× with a standard blond dye) was measured using appropriate equipment. The previously produced coloring formulations were then applied to the measured hair strands (Kerling) (solution ratio 4:1, 4 g cream per g hair) and allowed to act for 30 minutes. The hair strands were subsequently rinsed out and dried. The dried hair strands were measured a second time in the luster apparatus.

The luster apparatus is a luster chamber provided with a light-absorbing lining. The hair strands to be measured were clamped onto a cylinder and positioned in the middle of the luster chamber. As the illumination source, a rod-shaped gas discharge lamp which illuminated the hair strands, clamped onto the cylinder, through a small aperture was situated above the cylinder. The luster curve of each strand was measured using a digital camera and evaluated by image analysis. The luster value of the strands (L) was subsequently calculated according to the Reich and Robbins formula (1):

$$L_{Reich/Robbins} = \frac{S}{D * W_{1/2}}$$

L: luster
S: directed reflection
D: diffuse reflection
W½: half-width of the luster curve
(1) C. Reich and C. C. Robbins, J. Soc. Cosmet. Chem. 44, 221-234 (1993)

The change in luster was assessed by comparing the luster values measured before and after application of the agent according to the invention. Statistical methods were used to calculate whether the change in luster was significant.

The following luster values were obtained in the measurements. The higher the luster value, the higher the luster.

| Formulation | Luster value before dyeing | Luster value after dyeing | Increase in the luster value (Quotient of luster after dyeing/luster before dyeing) |
|---|---|---|---|
| V1 | 0.0017 | 0.0018 | 1.06 |
| V2 | 0.002 | 0.0075 | 3.75 |
| V3 | 0.002 | 0.0056 | 2.8 |
| V4 | 0.002 | 0.0092 | 4.6 |
| E1 | 0.002 | 0.0147 | 7.35 |
| E2 | 0.002 | 0.0143 | 7.15 |
| E3 | 0.002 | 0.0140 | 7.00 |
| E4 | 0.002 | 0.0174 | 8.7 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Agent for dyeing keratinic fibers, in particular human hair, containing in a cosmetic carrier
   (a) at least one cationic anthraquinone derivative of formula (I)

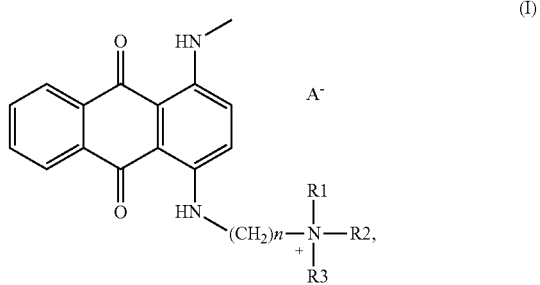

wherein
R1, R2, R3 independently stand for a $C_1$-$C_6$ alkyl group,
n stands for an integer from 2 to 8, and
A stands for a physiologically acceptable anion, (b) at least one further cationic direct dye which is different from formula (I),
(c) at least one amphoteric and/or zwitterionic surfactant, and
(d) at least one cationic polymer
wherein the one or more cationic anthraquinone derivatives of formula (I) comprises 0.0005% to 0.5% by weight, based on the total weight of the agent.

2. An agent according to claim 1, wherein R1 and R2 each stand for a methyl group, R3 stands for an n-propyl group, and n stands for the numbers 2 or 3.

3. An agent according to claim 1, wherein the one or more cationic anthraquinone derivatives of formula (I) comprises 0.05% to 0.3% by weight based on the total weight of the agent.

4. An agent according to claim 1, wherein the one or more cationic anthraquinone derivatives of formula (I) comprises 0.10% to 0.35% by weight based on the total weight of the agent.

5. An agent according to claim 1, wherein the cationic direct dye(s) (b) which is different from formula (I) is selected from the group consisting of: basic yellow 87, basic orange 31, basic red 51, basic violet 2, cationic blue 347 and combinations thereof.

6. An agent according to claim 1, wherein the cationic direct dye(s) (b) which is different from formula (I) is selected from the group consisting of: basic yellow 87, basic orange 31, basic red 51, basic violet 2, and combinations thereof.

7. An agent according to claim 1, wherein the cationic direct dye(s) (b) which is different from formula (I) comprises, in total quantity, 0.0005% to 0.55% by weight based on the total weight of the agent.

8. An agent according to claim 1, wherein the cationic direct dye(s) (b) which is different from formula (I) comprises, in total quantity, 0.005% to 0.40% by weight based on the total weight of the agent.

9. An agent according to claim 1, wherein the cationic direct dye(s) (b) which is different from formula (I) comprises, in total quantity, 0.025% to 0.30% by weight based on the total weight of the agent.

10. An agent according to claim 1, wherein the cationic direct dye(s) (b) which is different from formula (I) comprises, in total quantity, 0.05 to 0.20% by weight based on the total weight of the agent.

11. An agent according to claim 1, wherein the at least one amphoteric and/or zwitterionic surfactant is selected from the group consisting of: betaines, N-alkyl-N,N-dimethylammonium glycinates, N-acylaminopropyl-N,N-dimethylammonium glycinates, 2-alkyl-3-carboxymethyl-3-hydroxyethyl imidazolines, N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids.

12. An agent according to claim 1, wherein the amphoteric and/or zwitterionic surfactant includes a compound of formula (II) and/or of formula (III),

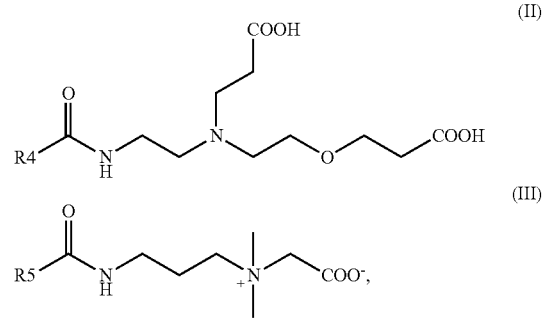

wherein
R4, R5 in each case independently stand for a saturated or unsaturated, branched or unbranched $C_8$-$C_{24}$ alkyl group.

13. An agent according to claim 1, wherein the one or more amphoteric and/or zwitterionic surfactants (c) comprises, in a total quantity, of 0.1% to 4.0% by weight based on the total weight of the agent.

14. An agent according to claim 1, wherein the one or more amphoteric and/or zwitterionic surfactants (c) comprises, in total quantity, 0.4% to 1.8% by weight based on the total weight of the agent.

15. An agent according to claim 1, wherein the at least one cationic polymer is selected from the group consisting of: polyquaternium-2, polyquaternium-5, polyquaternium-6, polyquaternium-7, polyquaternium-8, polyquaternium-9, polyquaternium-11, polyquaternium-16, polyquaternium-28, polyquaternium-32, polyquaternium-33, polyquaternium-44, polyquaternium-46, polyquaternium-55, and polyquaternium-68.

16. An agent according to claim 1, wherein the at least one cationic polymer comprises, in a total quantity, 0.1 to 2.0% by weight based on the total weight of the agent.

17. An agent according to claim 1, wherein the at least one cationic polymer comprises, in total quantity, 0.3 to 0.9% by weight based on the total weight of the agent.

18. An agent according to claim 1, wherein the agent includes polyquaternium-6 as a cationic polymer in a quantity of 0.0001 to 10% by weight based on the total weight of the agent.

19. An agent according to claim 1, wherein the agent includes polyquaternium-6 as a cationic polymer in a quantity of 0.01 to 5% by weight based on the total weight of the agent.

* * * * *